United States Patent [19]

Chu

[11] Patent Number: 5,200,514
[45] Date of Patent: Apr. 6, 1993

[54] SYNTHESIS OF 2-'DEOXYPYRIMIDINE NUCLEOSIDES

[75] Inventor: Chung K. Chu, Athens, Ga.

[73] Assignee: University of Georgia Research Foundation, Inc., Athens, Ga.

[21] Appl. No.: 467,152

[22] Filed: Jan. 19, 1990

[51] Int. Cl.$^5$ ............................................... C07H 1/00
[52] U.S. Cl. ............................... 536/28.53; 536/124; 536/28.4; 536/28.2; 536/28.5
[58] Field of Search .......................................... 536/23

[56] References Cited

U.S. PATENT DOCUMENTS 3,282,921  11/1966  Verheyden et al. .................. 536/23
3,687,931  8/1972   Verheyden et al. .................. 536/23
3,817,982  6/1974   Verheyden et al. .................. 536/23
4,904,770  2/1990   Starrett et al. ....................... 536/23

FOREIGN PATENT DOCUMENTS 0224390  7/1989  Japan .

OTHER PUBLICATIONS

Fukukawa et al., Chemical Abstracts vol. 100:22946y, 1984.
Lin, et al., *J. Med. Chem.*, 26 544 (1983).
Mansuri, et al., *J. Org. Chem.*, 54, 4780–4785 (1989).
Marumoto, et al., *Chem. Pharm. Bull.*, 22(1), 128 (1974).
Merger, et al., *Appl. Radiat. Isot.*, vol. 37, No. 7, 613 (1986).
Ozaki, et al., *Bulletin of the Chemical Society of Japan*, vol. 50(8), 2197 (1977).
Reichman, et al., *Carbohydrate Research*, 42, 233–240 (1975).
Ritzmann et al., *Carbohydrate Research*, 39 227–236 (1975).

*Primary Examiner*—John W. Rollins
*Assistant Examiner*—J. Oliver Wilson
*Attorney, Agent, or Firm*—Kilpatrick & Cody

[57] ABSTRACT

A method for the preparation of 2'-deoxynucleosides and 2',3'-dideoxy-2',3'-didehydronucleosides that includes the step of reacting a nucleoside having hydroxyl groups in the 2' and 3' positions with a mixture of acyl bromide or chloride and HX, wherein X is Br or Cl, at moderate temperature, to give a haloacyl nucleoside derivative that can be deprotected and reduced to form the desired compound.

13 Claims, 3 Drawing Sheets

X = O, NH
Ac = acetyl

Ac = acetyl

Ac = acetyl

SYNTHESIS OF 2-DEOXYPYRIMIDINE NUCLEOSIDES

This invention is in the area of synthetic organic chemistry, and is in particular an economical, efficient and convenient method for the preparation of 2'-deoxynucleosides and 2',3'-dideoxy-2',3'-didehydronucleosides.

Since the initial discovery of the antiviral activity of 3'-azido-3'-deoxythymidine (AZT) against human immunodeficiency virus (HIV) (Mitsuya, H., et al., *Proc. Natl. Acad. Sci. U.S.A.* 82, 7096 (1985)), a number of deoxynucleosides have been found to possess potent anti-HIV activity in vitro, including 3'-azido-2',3'-dideoxyuridine (alternatively named AzddU, AZDU or CS-87), and 3'-azido-5-ethyl-2',3'-dideoxycytidine (AzddMeC). Nucleosides with potent antibiotic activity are also well known. The active antiviral and antibiotic nucleosides all exist in a β-anomeric configuration (i.e., the base is bonded to the 1-position of the sugar through a β bond).

2',3'-Dideoxynucleosides have historically been prepared by either of two routes; condensation of a sugar moiety with a nitrogenous base, and derivatization of a preformed nucleoside. The reported methods of preparation are generally suitable for laboratory syntheses to obtain small amounts of compound for experimental use, but are not well suited for industrial scale preparation of the compounds.

Synthetic schemes for the preparation of nucleoside derivatives that include the step of condensing a sugar with a nitrogenous base are described in U.S. Pat. No. 4,230,689 to Bobek, et al. and by Fleet, Son and Drome, *Tetrahedron* 42(2), 625 (1988).

A novel synthesis of AZDU from an α,β-unsaturated τ-butyrolactone has been described by Chu, C. K., Beach, J. W., Ullas, G. V., and Kosugi, Y., in *Tetrahedron Lett.* 29, 5349 (1988). In this synthetic scheme, the azide moiety is introduced into the lactone through a Michael reaction to obtain a derivatized carbohydrate, which is then condensed with a silylated uridine to form the derivatized nucleoside. In this reaction scheme, however, glycosylation yields a mixture of 2 to 1 β anomer to α anomer, reducing the efficiency of reaction.

Because of the difficulty in directing stereoisomerism in a nucleoside reaction scheme that includes condensation of a base with a sugar, this route may not be desirable for industrial manufacture of commercial nucleosides. It appears that a reaction scheme that derivatizes a preformed nucleoside is a more economically viable route for the preparation of these compounds.

Synthetic schemes for the preparation of nucleoside derivatives from preformed nucleosides include those described by: Dyatkina, N. B., *Soviet J. Bioro. Chem.* 12, 563 (1986); Colla, et al., *Eur. J. Med. Chem.—Chim. Ther.* 20(4), 295 (1985); Herdewijn, et al., *J. Med. Chem.* 30, 1270 (1987); Horowitz, et al., *J. Org. Chem.* 29, 2076 (1984); Krenitsky, et al., *J. Med. Chem.* 26(6), 891 (1983); and Webb, et al., *Nucleosides and Nucleotides* 7(2), 147 (1988).

The original synthesis of AZDU was reported by Lin and Mancini, starting from 2'-deoxyuridine. Lin, T. S., and Mancini, W. R., *J. Med. Chem.* 26, 544 (1983). The first step in the Lin scheme is the mesylation of the 3'-position of a 5'-protected-2'-deoxynucleoside. Treatment with base provides the 2,3'-anhydro nucleoside derivative, that is acidified and again mesylated to form the 1-[2-deoxy-3-O-methanesulfonyl-5-O-(protected)-β-D-threo-pentofuranosyl]nucleoside. This compound is then reacted with azide ion and then deprotected to produce a 3'-azido-2',3'-dideoxynucleoside.

While the Lin and Mancini reaction scheme is suitable for the industrial preparation of 3'-substituted-2',3'-dideoxynucleosides, it is limited because the starting material, 2'-deoxynucleoside, is difficult to obtain and prohibitively expensive.

Several synthetic methods for 2'-deoxyuridine or related compounds have been reported in the literature: Ozaki, S., et al., *Bull. Chem. Soc.* (Japan) 50, 2197 (1977); Greenberg, S., and Moffatt, J. G., *J. Am. Chem. Soc.* 1073, 4016; Robins, M. J., and Wilson, J. S., *J. Am. Chem. Soc.* 103, 933 (1981); and Marumoto, R., and Honjo, M., *Chem. Pharm. Bull.* (Japan) 22, 128 (1974).

Ozaki et al. report that a uridine nucleoside can be reacted with propionyl bromide to form a 3',5'-di-O-propionyl-2'-bromo- 2'-deoxyuridine, that can be reduced and deprotected to form a 2'-deoxyuridine. While Ozaki states that this synthesis is suitable for industrial preparation of 2'-deoxynucleosides, the method uses large quantities of propionyl bromide (a six molar excess), which is an expensive reagent.

Greenberg and Moffatt report that α-acetoxyisobutyryl bromide or chloride can be reacted with a nucleoside to obtain 2'-chloro- or 2'-bromo-2'-deoxyuridine, which can be reductively dehalogenated to 2'-deoxyuridine. As with the Ozaki synthesis, however, the synthetic scheme requires large quantities of reagent, α-acetoxyisobutyryl halide, which is expensive when used on an industrial scale.

Marumoto and Honjo react acetyl bromide with uridine in acetonitrile to produce 2'-halogeno-2'-deoxyuridine. The product mixture contains 3',5'-di-O-acetyl-2'-bromo-2'-deoxyuridine and 2',3',5'-tri-O-acetyluridine along with unreacted uridine. The mixture of products obtained in the Marumoto procedure results in decreased efficiency of reaction, reducing suitability for industrial use.

Mansuri et al., at Bristol-Myers Corporation, developed a synthetic method for the preparation of 2',3'-unsaturated nucleosides that includes reacting a nucleoside with 2-acetoxyisobutyryl bromide (approximately three equivalents) to form a 5'-O-protected-3'-aceto-2'-bromo-nucleoside, in a reported 67% yield. Mansuri, et al., *J. Org. Chem,* 54, 4780 (1989). This product is stirred with activated Zn/Cu to produce the corresponding olefin in a reported 40% yield Mansuri et al. did not prepare any 2'-deoxynucleoside derivatives. Further, the yield of the reaction is not suitable for an industrial scale preparation. To force the acetyl bromination reaction to a higher yield (greater than 67%), a large excess of acetoxyisobutyryl bromide or acetyl bromide is required, greatly increasing the cost of reaction. Further, the Mansuri reaction is carried out at reflux (approximately 80° C. for acetyl bromide), that tends to increase the number of undesirable side reactions.

Unfortunately, as described above, the published synthetic schemes for 2'-deoxynucleosides are inefficient or are not easily scaled up for industrial preparation. The inability to prepare this starting material for important biologically active nucleosides in an efficient manner results in shortages of commercial compounds and high health care costs. Further, the high cost of the pharmaceutical nucleosides increases the personal tribulation of those needing treatment.

There is a strong need for a method of synthesis of 2'-deoxynucleosides that can be used in an industrial scale preparation of biologically active nucleosides.

It is therefore an object of the present invention to provide a method of synthesis of 2'-deoxynucleosides that is economical as well as efficient and convenient.

It is another object of the present invention to provide a method of synthesis of 2'-deoxynucleosides that can be carried out on an industrial scale.

SUMMARY OF THE INVENTION

The claimed invention is an economical method of synthesis of 2'-deoxynucleosides, a starting material for a variety of pharmaceutically important nucleosides. The method is well suited for industrial manufacture because it minimizes the use of necessary reagents and can be carried out at moderate temperature, minimizing unwanted side reactions. The method produces a high yield of product.

The method includes reacting a nucleoside having hydroxyl groups in the 2' and 3' positions with a mixture of acyl bromide or chloride and HX, wherein X is Br or Cl, at moderate temperature, to give a 3',5'-O-diacyl-2'-(bromo or chloro)-2'-deoxynucleoside in excellent yield (greater than 95% for the preparation of 2',3'-O-diacyl-2'-bromouridine). The reaction is performed in acetic acid or other suitable organic solvent. The 3',5'-O-diacyl-2'-(bromo or chloro)-2'-deoxynucleoside is then reduced with tributyltin hydride or by other catalytic means to produce a 3', 5'-O-diacyl-2'-deoxynucleoside in high yield.

Tributyltin hydride can be prepared in situ from tributyltin chloride and sodium borohydride, which substantially decreases the cost of that reagent in this method.

Deprotection of the 3',5'-O-diacyl-2'-deoxynucleoside provides a high yield of the 2'-deoxynucleoside product.

The disclosed invention can also be used to economically prepare a 2',3'-dideoxy-2',3'-didehydronucleoside, including a thymidine, in high yield. As an example, 5-methyl uridine is reacted with an acyl bromide or chloride and HX to give 3',5'-O-diacyl-2'-halo-2'-deoxyuridine. The 3',5'-O-diacyl-2'-halo-2'-deoxyuridine is then unsaturated by methods known to those skilled in the art, including treatment with chromous acetate, zinc/acetic acid, or Zn/Cu, to give the thymidine derivative.

A nucleoside that has a base other than pyrimidine can be reacted with a mixture of acyl bromide or chloride and HX at moderate temperature to give a mixture of 2'-halo-3'-acyl and 2'-acyl-3'-halonucleosides. This mixture can be converted to the corresponding olefin by methods known to those in the art, including treatment with chromous acetate, zinc/acetic acid or Zn/Cu.

The unsaturated nucleosides made according to this invention can be hydrogenated by conventional methods to form 2',3'-deoxynucleosides.

DETAILED DESCRIPTION OF THE INVENTION

The present invention is an economical method of synthesis of 2'-deoxynucleosides and 2',3'-dideoxy-2',3'-didehydronucleosides that is well suited for the industrial manufacture of these compounds. The key feature of the present method is the use of a mixture of acyl bromide or chloride and HX, wherein X is Br or Cl, at moderate temperature, to form a haloacetate nucleoside derivative that can later be reduced to a 2'-deoxynucleoside or to a 2',3'-dideoxy-2',3'-didehydronucleoside. The use of an acyl halide and HX to form the haloacetate intermediate reduces the cost of preparation of 2'-deoxynucleosides and 2',3'-dideoxy-2',3'-didehydronucleosides by reducing the amount of reagent needed to form the intermediate in high yield.

The method also minimizes the cost of preparing 2'-deoxynucleosides by preparing tributyltin hydride in situ from tributyltin chloride and sodium borohydride. The in situ preparation of tributyltin hydride has been reported by Corey and Suggs in *J. Org. Chem.* 40, 2554 (1975).

Figure 1:
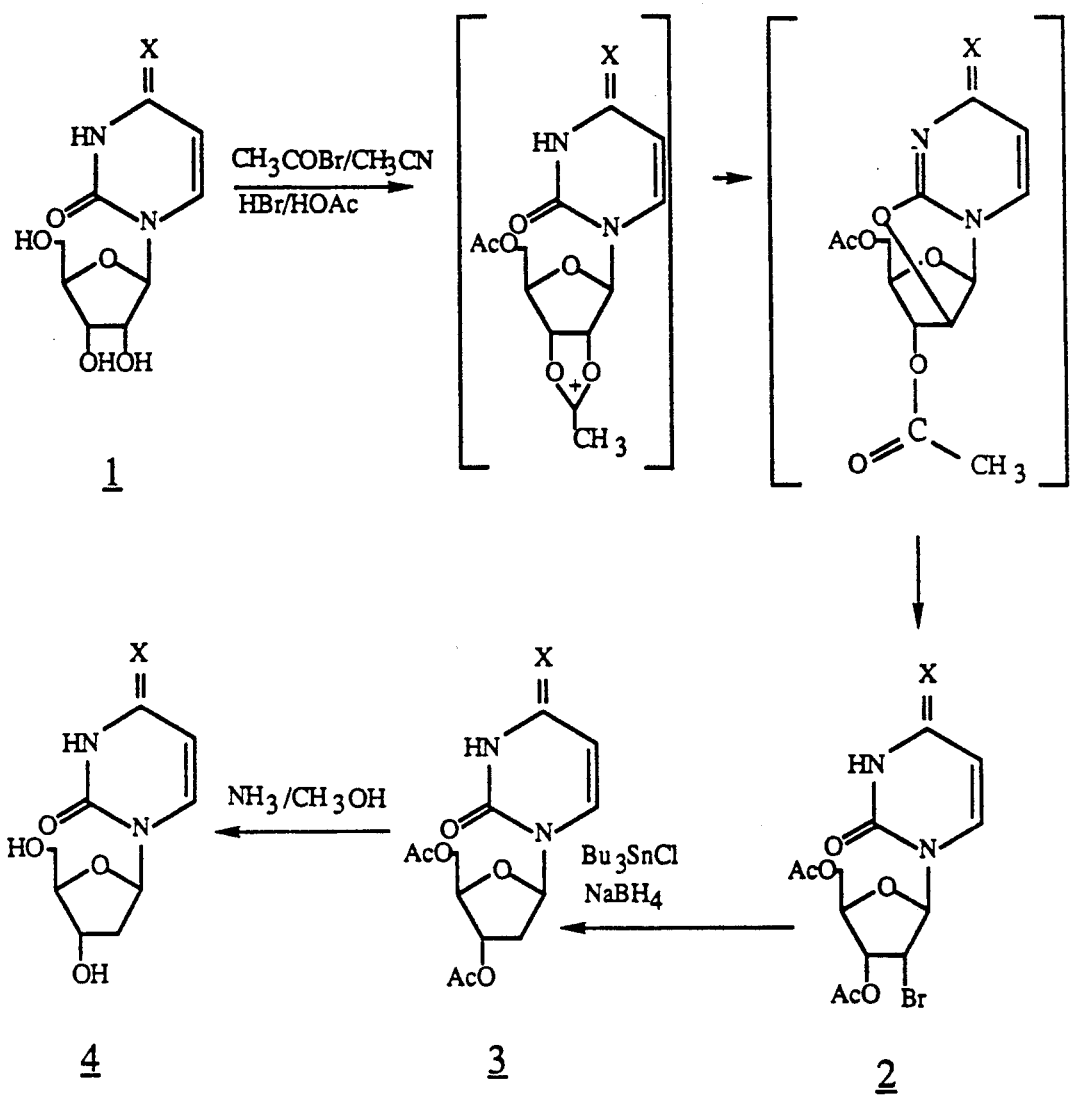
FIG. 1 is an illustration of the mechanism of reaction of acetyl bromide and HBr with uridine and cytidine.

In one embodiment, as shown in FIG. 1, the claimed invention is an efficient and convenient method of synthesis of 2'-deoxynucleosides, a starting material for a variety of pharmaceutically important 3'-substituted nucleosides. The synthetic scheme involves reacting a nucleoside with acyl bromide or chloride and HX at moderate temperature to form a 3',5'-O-diacyl-2'-halonucleoside. The 2'-halogen is then removed by reduction with tributyltin hydride, or hydrogen in combination with another catalytic agent, including palladium on carbon, or palladium on barium sulfate. After reduction, the 3',5'-diacyl groups can be removed with a base, for example, methanolic ammonia or sodium hydroxide.

The method of preparation of 2'-deoxynucleosides is applicable to any natural or synthetic nucleoside that has hydroxyl groups in the 2' and 3'-positions and that has a functional group in the base that is capable of reacting with the initially formed charged cyclic intermediate to provide an intermolecular bond with the 2'-position of the sugar (See FIG. 1). Pyrimidine nucleosides are suitable because the 2-carbonyl group can attack the 2'-position of the sugar to form a 2,2'-anhydro intermediate.

2'-Deoxyuridines and 2'-deoxycytidines prepared according to this route can be used in the synthesis of 3'-substituted-2',3'-dideoxynucleosides, such as AZdU and AZT, through the Lin et al. mesylation scheme.

Figure 2:
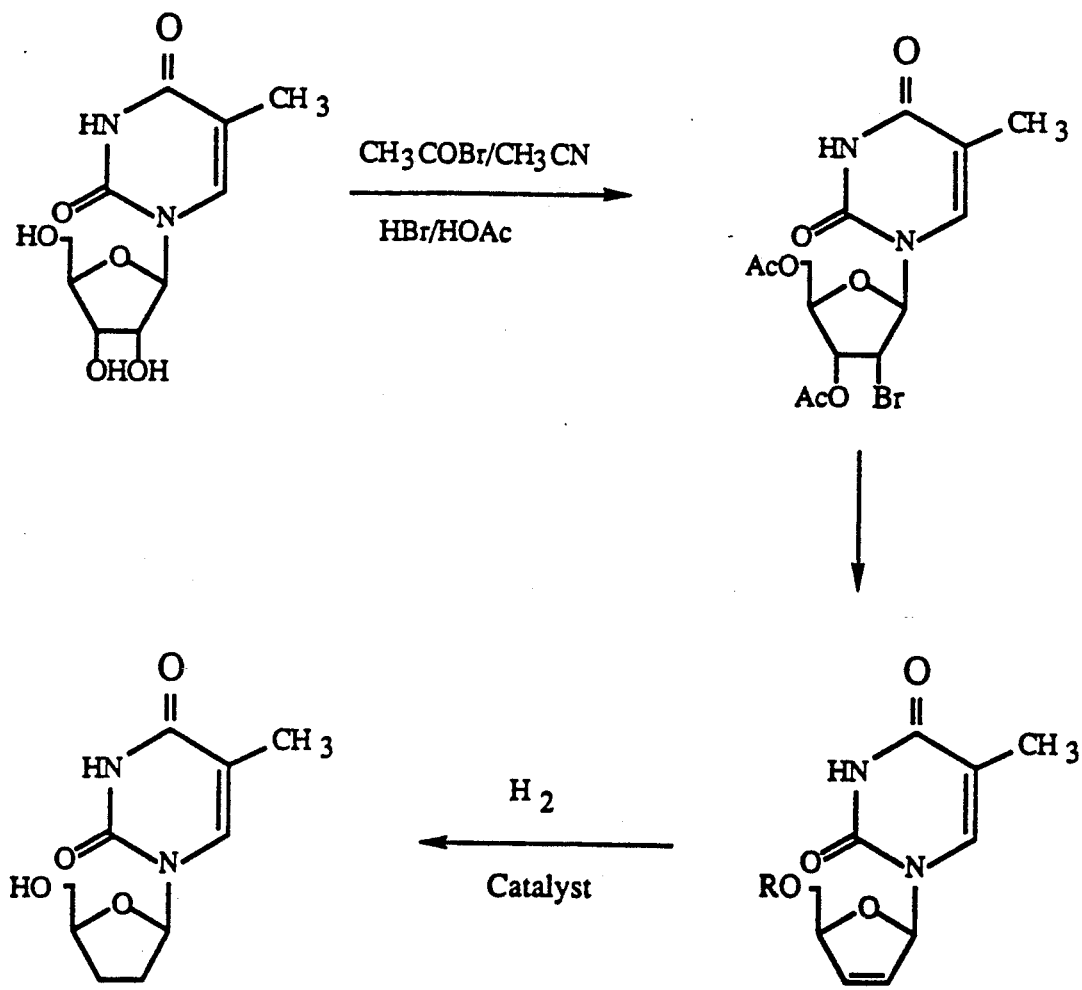
FIG. 2 is an illustration of the reaction scheme for the method of preparation of a 2',3'-dideoxy-2',3'-didehydro or 2',3'-dideoxythymidine.

In another embodiment, any nucleoside with cis hydroxyl groups in the 2' and 3' positions, regardless of the nature of functional groups in the base, can be reacted with an acyl halide and HX to form a 2',3'-haloacyl compound (which can include a mixture of 2'-halo-3'-acyl and 2'-acyl-3'-halo derivatives) that can be reduced to the corresponding 2',3'-dideoxy-2',3'-didehydronucleoside. For example, as shown in FIG. 2, the claimed invention provides a practical and inexpensive route to 2',3'-dideoxy-2',3'-didehydrothymine (D4T), which can be hydrogenated to the corresponding 2',3'-dideoxythymine (D2T).

The base in the nucleoside can be one found in a naturally occurring nucleoside, such as a purine or pyrimidine, or can be a non-naturally occurring base such as a pyrrole, indole, imidazole, pyrazole, quinazoline, pyridazine, pyrazine, cinnoline, phthalazine, quinoxaline, xanthine, hypoxanthine, pterdine, 5-azacytidine, 5-azauracil, triazolopyridine, imidazolopyridine, imidazolotriazine, pyrrolopyrimidine, or pyrazolopyrimidine. The base can also be an oxygen heterocycle, such as oxazole or isooxazole, or an oxygen-sulfur heterocycle such as thiophene or benzothiophene, or a sulfur-nitrogen heterocycle such as thiazole or isothiazole.

In this method, between approximately 1 and 5 equivalents of acyl bromide or chloride is used. The prefered range is between 2 and 3 equivalents. The amount of HX used will depend on the amount of acyl bromide or chloride used; the less acyl halide used, the more HX needed to push the reaction to completion. A preferred range of HX is 0.5 to 5 equivalents. A more preferred range of HX is 1 to 3 equivalents.

The use of acetyl halide and α-acetoxyisobutyryl halide to form a 3'-acetyl-2'-halo-nucleoside is known. However, a large excess of the acetyl halide or α-acetoxyisobutyryl halide has been required in prior synthetic schemes to force a high yield of product. The excess reagent needed substantially increases the cost of reaction.

As stated above, HBr and HCl are sources of halide ions that are less expensive than organic halides, such as acetyl bromide or α-acetoxyisobutyryl bromide. The inclusion of HBr or HCl in the reaction of a nucleoside with an acyl halide greatly increases the yield of bromoacetate nucleoside product by forcing the reaction to completion with excess halide ion, without the expense of using excess costly organic reagents. For example, the use of 1.2 equivalents of HBr in combination with approximately 3 equivalents of acetyl bromide produces a 3',5'-O-diaceto- 2'-bromouridine in almost quantitative yield. The efficiency of reaction substantially decreases the cost of industrial preparation of 2'-deoxynucleosides and 2',3'-unsaturated nucleosides.

Acyl halides suitable for use in this method include, but are not limited to: $C_1$ to $C_{20}$ alkanoic bromides or chlorides, including acetyl bromide, acetyl chloride, propionyl bromide, and propionyl chloride; acetoxyisobutyryl bromide, and acetoxyisobutyrl chloride. Contemplated equivalents include any compound that will effectively perform the function of the acyl halide described herein.

HX can be introduced into the reaction in solution with the acyl halide, or can be bubbled through as a gas. It can also be generated in situ by the reaction of other compounds, for example, an organic halide and water.

Acyl bromide and HBr are the preferred reagents in this method, because of the ease of elimination of the Br ion. Elimination of the Cl ion is slower and somewhat more difficult than elimination of Br. It is preferable not to mix halides in the reaction; acyl bromides are preferably used in combination with HBr and acyl chlorides in combination with HCl.

The reaction can be performed in any suitable organic solvent, including acetic acid, acetonitrile, and methylene chloride. Alternatively, the acyl bromide or chloride can be used as the solvent if it has suitable melting and reflux characteristics. Water can be added to the acyl bromide or chloride solvent to produce hydrogen chloride or bromide in situ.

The reaction can be performed at a temperature between room temperature and the reflux temperature of the solvent chosen. It is preferably performed below the reflux temperature of the solvent to minimize unwanted side reactions. A prefered temperature range is between 50° and 60° C.

The method of the present invention is described with reference to the following non-limiting examples. As characterized below, the methods are applicable to a wide variety of starting materials and final products.

EXAMPLE 1: PREPARATION OF 2'-DEOXYURIDINE AND 2'-DEOXYCYTIDINE FROM URIDINE OR CYTIDINE WITH ACETYL BROMIDE AND HBr

A mixture of acetyl bromide and HBr can be used to prepare 2'-bromo-3'-acetyl uridine or cytidine from the corresponding nucleoside in almost quantitative yield. The acetyl bromide initially reacts with the vicinal diol of the nucleoside to form a charged cyclic intermediate, as shown in FIG. 1. The 2-carbonyl group of the nucleoside attacks the 2'-position of the nucleoside, forming a 2,2'-anhydro bond. The bromo anion then replaces the 2'-anhydro bond in an $SN_2$ reaction, forming a 2'-bromo-3'-acetyl nucleoside.

A. 2'-Deoxyuridine

An important application of this invention is in the industrial manufacture of AZDU (3'-azido-2',3'-dideoxyuridine), a potent antiviral agent that inhibits replication of human immunodeficiency virus (HIV), the etiological cause of acquired immune deficiency syndrome (AIDS).

For example, addition of excess acetyl bromide (3.2 eq) plus 30% HBr in acetic acid (1.2 eq) to uridine at 55°-60° C. gave the desired 3',5'-di-O-acetyl-2'-bromo-2'-deoxyuridine 2 (FIG. 1; X=O in uridine and uridine derivatives) in excellent yield (>95%). 3',4'-Di-O-acetyl-2'-bromo-2'-deoxyuridine 2 was then reduced to 3 by tributyltin hydride (provided either as the premade compound or prepared by in situ generation through the reaction of tributyltin chloride with sodium borohydride) in absolute ethanol in excellent yield (>95%). 2',3'-Di-O-acetyl-2'-deoxyuridine was treated with methanolic ammonia to obtain an excellent yield of 2'-deoxyuridine. The overall yield of this process was 72–76% without chromatography.

The following is a detailed working example for the preparation of 2'-deoxyuridine. Melting points were determined on a Thomas Hoover capillary apparatus and are uncorrected. $^1$H NMR spectra were recorded on a JEOL FX 90Q fourier transform spectrometer, using $(CH_3)_4Si$ as the internal standard. Chemical shifts are reported in parts per million (δ) and signals are described as a s (singlet), d (doublet), t (triplet), q (quartet), or m (multiplet). UV spectra were obtained on a Beckman DU-7 spectrophotometer. Optical rotations were measured on a Perkin-Elmer 141 polarimeter. Thin layer chromatography ("TLC") was performed on Uniplates (silica gel) purchased from Analtech Co. Elemental analyses were performed by Atlantic Microlab Inc., Norcross, Ga.

3',5'-Di-O-acetyl-2'-bromo-2'-deoxyuridine (2)

Acetyl bromide (165 g, 1.34 mol) was added dropwise to a suspension of uridine 1 (100 g, 0.409 mol) in a mixture of hydrobromic acid (100 mL, 30% wt. solution in acetic acid) and dry acetonitrile (2.5 L, dried over 4 Å molecular sieves) at 55°-60° C. The solution was stirred for approximately 2 hours. The homogeneous solution turned dark brown after addition of approximately half of the acetyl bromide. The solution was heated for another 3 hours at 60° C. The solvent was then removed under reduced pressure. The resulting syrup was dissolved in ethyl acetate (1 L) and washed with saturated sodium bicarbonate solution. The organic layer was washed with brine and water successively and then the aqueous layer was extracted with ethyl acetate (250 mL×3). The combined organic layers were dried (Na$_2$SO$_4$) and the solvent was removed to obtain a syrup, which was co-evaporated twice with toluene to provide 2 as a foam which was used for the next reaction without further purification. An analytical sample was obtained by preparative TLC (CHCl$_3$:CH$_3$OH, 10:1) to yield 2 as a crystalline solid, mp. 69°-77° C.; UV(CH$_3$CH$_2$OH) $\lambda_{max}$ 258 nm ($\epsilon$ 9450); IR (KBr) $\lambda_{max}$: 1750, 1690, 1450, 1380, 1230 cm$^{-1}$; NMR (CDCl$_3$): $\delta$ 2.14 (3 H, s, —OCOCH$_3$), 2.18 (3 H, s, —OCOCH$_3$), 4.39 (3 H, m, H$_{4'}$, 2H$_{5'}$), 4.64 (1 H, t, J=5.86 Hz, H$_{2'}$), 5.15 (1 H, m, H$_{3'}$), 5.82 (1 H, d, J=8.2 Hz, H$_5$), 6.23 (1 H, d, J=5.86 Hz, H$_{1'}$), 7.48 (1 H, d, J=8.2 Hz, H$_6$), 10.02 (1 H, bs, HN).

3',4'-Di-O-acetyl-2'-deoxyuridine (3)

Method A. Compound 2 was dissolved in dry toluene (1.2 L, dried over 4 Å molecular sieves) at 60° C. Tributyltin hydride (186 g, 0.639 mol) was added followed by AIBN (azobisisobutyronitrile; 16 g). The mixture was heated at 105°-110° C. for 3 hours and then kept at room temperature overnight. The solvent was removed under vacuum to obtain a syrup that was dissolved in acetonitrile (1 L). The solution was washed with hexanes (1 L). The hexane layer was extracted with acetonitrile (500 mL×2). The combined acetonitrile extracts were concentrated to a syrup, that was used in the next reaction without further purification. A small portion of the crude product was purified by preparative TLC (CHCl$_3$:CH$_3$OH, 10:1) for identification. UV(CH$_3$OH) $\lambda_{max}$ 260 nm: IR (KBr) $\lambda_{max}$ 1750, 1695, 1465, 1370, 1270 cm$^{-1}$; NMR (CDCl$_3$): $\delta$ 2.13 (6 H, s, —OCOCH$_3$), 2.25-2.68 (2 H, m, H$_{2'}$), 4.27-4.34 (3 H, m, H$_{4'}$, 2H$_{5'}$), 5.28 (1 H, m, H$_{3'}$), 5.81 (1 H, d, J=8.2 Hz, H$_5$), 6.29 (1 H, dd, J=8.2 Hz, 5.86 Hz, H$_{1'}$), 7.53 (1 H, d, J=8.2 Hz, H$_6$), 10.00 (1 H, bs, HN). Anal. Calcd. for C$_{13}$H$_{16}$N$_2$O$_7$.0.5H$_2$O; C, 48.60; H, 5.33, N, 8.72. Found: C, 48.66; H, 5.31; N, 8.73.

Method B. The same amount of compound 2 was dissolved in absolute alcohol (1.2 L) at 65° C. Tributyltin chloride (40 g, 0.123 mol) was added followed by sodium borohydride (23.4 g, 0.618 mol). The mixture was stirred at reflux for 20 minutes, and then cooled to 60° C. Oxalic acid (3 g) was added while stirring the solution for another hour. The mixture was then concentrated to 600 mL and the precipitates formed were filtered off. The filtrate was concentrated to a syrup that was triturated with 1 L of chloroform. The copious, colorless precipitate that formed was filtered off. The solvent was removed under vacuum to obtain a syrup, that was used in the next reaction without further purification.

2'-Deoxyuridine (4)

A solution of compound 3 (from method A) in a saturated solution of methanolic ammonia (670 g) was stirred at room temperature for 48 hours. The solvent was then removed under vacuum to obtain a syrup that was dissolved in acetonitrile (500 mL) and washed with hexanes (700 mL). The hexanes layer was extracted with acetonitrile (300 mL×2) and the combined acetonitrile extracts were concentrated under vacuum to a syrup. The syrup was dried under high vacuum to yield a semi-solid which on trituration with hexanes (0.5 L) and keeping at room temperature for 0.5 hours yielded a pale-yellow solid. The solvent was decanted and the solid was recrystallized from methanol (50 mL) to yield 4 as colorless crystals (38.2 g). The mother liquor was concentrated to a syrup, and passed through a short silica gel column using CHCl$_3$, CHCl$_3$:CH$_3$OH (10:1→10:2→10:3) as the eluent to get a second crop of 4 (29.8 g), overall yield was 68.0 g (72%, from uridine), mp. 163°-64° C. (Dekker, C. A. and Todd, A. R., *Nature* 166, 557 (1950), 163° C.). [$\alpha$]$_D$=+32° (c=0.668, H$_2$O) (Aldrich Catalog, 452 (1988), [$\alpha$]$_D$=+29.8° (c=2, H$_2$O). UV (0.1N HCl) $\lambda_{max}$ 264 nm ($\epsilon$ 21000), $\lambda_{min}$ 230 nm ($\epsilon$ 8800); (0.1N NaOH) $\lambda_{max}$ 216 nm ($\epsilon$ 37000), $\lambda_{min}$ 238 nm ($\epsilon$ 18000). The NMR and IR spectra were identical with that of an authentic sample of 2'-deoxyuridine.

Compound 3 from method B was treated as above giving 72 g of 4 (over-all yield 76%).

B. 2'-Deoxycytidine

2'-Deoxycytidine can be prepared in the same manner as 2'-deoxyuridine, using cytidine as the starting material in place of uridine. The N$^6$ amino group in cytidine does not have to be protected in the reaction. In general, the reaction of cytidine with the acetyl bromide/HBr mixture requires a slightly higher temperature and slightly more HBr than the corresponding uridine reaction.

The following is a detailed working example for the preparation of 3',5'-O-diacetyl-2'-bromo-cytidine. This compound can be reduced using the same procedure described above for 2'-deoxyuridine.

Acetyl bromide (16.5 g, 134 mmol, 3.3 eq.) was added dropwise over 0.5 hours to a suspension of cytidine (10 g, 41.1 mmol) in CH$_3$CN (250 mL) and HBr in acetic acid (10 mL, 30% weight) heated at 60°-65° C. The mixture was stirred at 100° C. for 3 hours, and then 10 mL more HBr in acetic acid was added. The mixture was stirred at 100° C. for an additional 28 hours. The solution was removed under vacuum to get a solid, which was purified with silica gel chromatography, to get 9.05 g of a solid (yield 56%).

EXAMPLE 2: PREPARATION OF OTHER 2',3'-DIDEOXY-2',3'-DIDEHYDRONUCLEO-SIDES

The method of synthesis described here can be used to prepare any 2',3'-unsaturated nucleoside. As shown in FIG. 2, the method can be used to decrease the cost of preparation of 2',3'-dideoxy-2',3'-didehydrothymidine (also referred to as 2',3'-unsaturated thymidine or 1-(2,3-dideoxy-$\beta$-D-glycero-pent-2-enofuranosyl)thymine), that can be used as is or reduced to produce 2',3'-dideoxythymidine.

5-Methyluridine, the starting material for the preparation of 2',3'-dideoxy-2',3'-didehydrothymidine, can be prepared by coupling 1-O-acetyl-2,3,5-tri-O-benzoyl-ribose and silylated thymine by methods known to those skilled in the art. Vorbruggen, H., Bennus, B., *Chem. Ber.*, 114, 1279 (1981).

5-Methyluridine is reacted with acetyl bromide and HBr under the same conditions as described above for the reaction of uridine with these reagents, to produce 3'-aceto-2'-bromo-5-methyluridine.

3'-Aceto-2'-bromo-5-methyluridine can be reduced to the 2',3'-dideoxy-2',3'-didehydronucleoside by methods known to those skilled in the art. For example, in the Verheyden method, the haloacetate is converted to the olefin by treatment with chromous acetate. Verheyden and Moffat, *J. Org. Chem.*, 37, 2289 (1972); Jain, et al., *J. Org. Chem.*, 39, 30 (1974). In the Classon method, zinc-/acetic acid is used as the reagent to form the unsaturated nucleoside from the haloacetate. Classon, et al., *Acta Chem. Scand.* B36, 251 (1983). The Robins method involves the use of a Zn/Cu coupling reagent to remove the haloacetate groups. Robins, et al., *Tet. Lett.* 25, 367 (1984).

If desired, the 2',3'-dideoxy-2',3'-didehydrothymidine can be reduced to the corresponding 2',3'-dideoxythymidine by methods known to those skilled in the art. For example, hydrogenation can be accomplished by bubbling $H_2$ gas through an ethanol solution containing 10% palladium on carbon under pressure.

Figure 3:
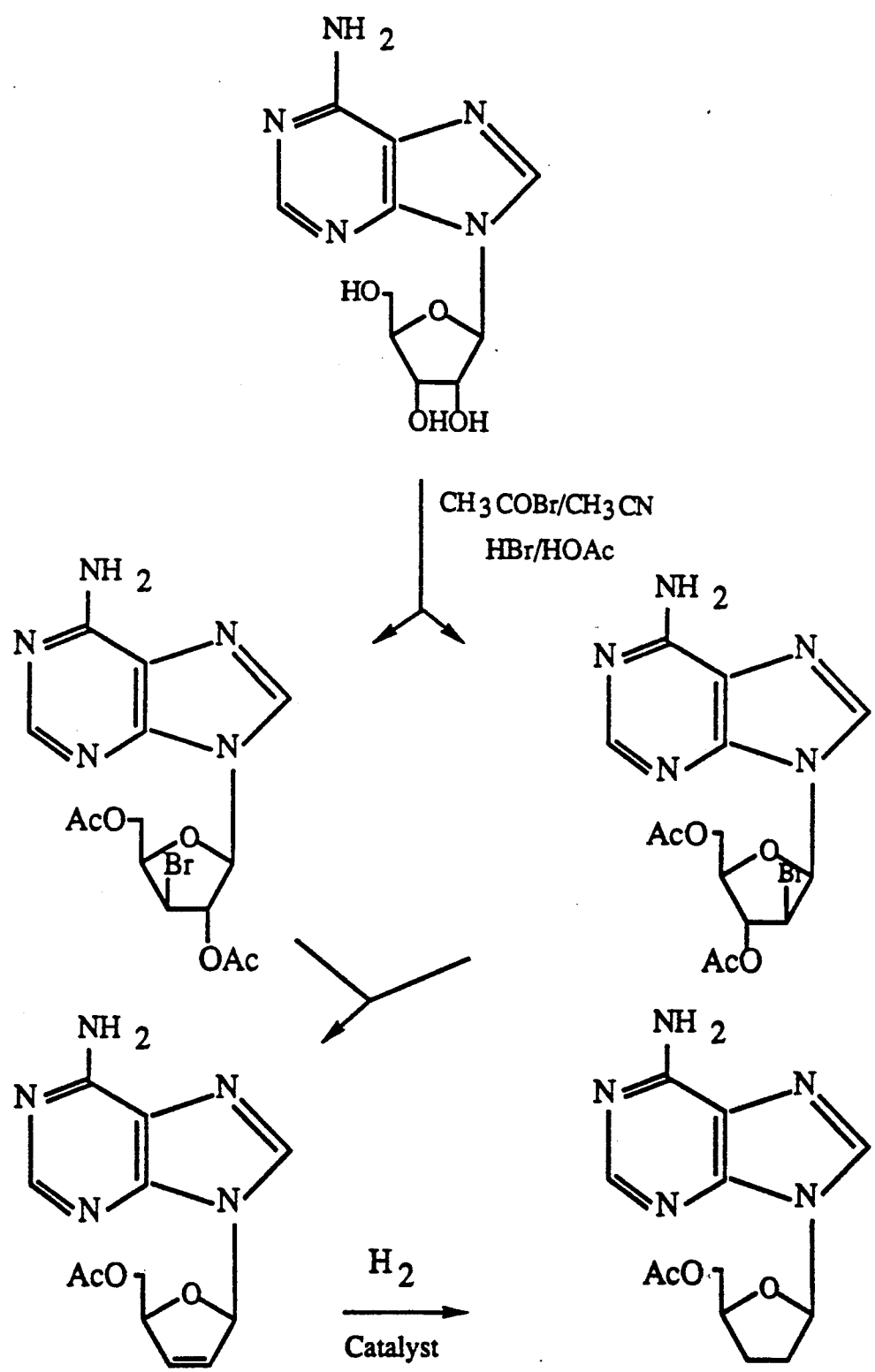
FIG. 3 is an illustration of the reaction scheme for the method of preparation of a 2',3'-dideoxy-2',3'-didehydro purine nucleoside.

As shown in FIG. 3, reaction of purine nucleosides with acetyl bromide/HBr results in a mixture of 3'-acetyl-2'-bromo-5'-acetyl and 2'-acetyl-5'-acetyl-3'-bromo nucleosides. This mixture of nucleosides can be reduced to the corresponding 2',3'-dideoxy-2',3'-didehydronucleosides by methods known to those skilled in the art, including those identified in Section B., above.

As with the 2',3'-dideoxy-2',3'-didehydrothymine nucleoside, the 2',3'-dideoxy-2',3'-didehydropurine nucleosides can be reduced to the corresponding 2',3'-dideoxythymidine by methods known to those skilled in the art. For example, hydrogenation can be accomplished by bubbling $H_2$ gas through an ethanol solution containing 10% palladium on carbon under pressure.

Modifications and variations of the method of preparation of 2'-deoxynucleosides and 2',3'-dideoxy-2',3'-didehydronucleosides will be apparent to those of skill in the relevant art from the foregoing detailed description. Such modifications and variations are intended to come within the scope of the following claims.

We claim:

1. A process for the preparation of a 2'-deoxy pyrimidine nucleoside, comprising the steps of:
    combining a nucleoside that has 2' and 3' hydroxyl groups with a mixture of acyl bromide or chloride selected from the group consisting of a $C_1$ to $C_{20}$ alkanoic bromide or chloride, acetoxyisobutyryl bromide, or acetoxyisobutyryl chloride, and HX, wherein X is Br or Cl, to form a 2'-halo-3'-acyl pyrimidine nucleoside, and then
    reacting the 2'-halo-3'-acyl pyrimidine nucleoside with a reducing agent to form a 2'-deoxy pyrimidine nucleoside.

2. The process of claim 1, further comprising selecting acetyl bromide.

3. The process of claim 1, wherein HX is HBr.

4. The process of claim 1, wherein the 2'-halo-3'-acyl pyrimidine nucleoside is 2'-bromo-3'-acetyluridine.

5. The process of claim 1, further comprising combining the nucleoside with a mixture of acyl bromide or chloride and HX in a solvent that includes acetic acid.

6. The process of claim 1, wherein the 2'-halo pyrimidine nucleoside is reduced with tributyltin hydride.

7. The process of claim 6, wherein the tributyltin hydride is prepared in situ with tributyltin chloride and sodium borohydride.

8. The process of claim 1, further comprising the step of adding a base to remove any acyl groups in the 3' or 5' positions.

9. The process of claim 8, wherein the base is selected from the group consisting of NaOH and methanolic ammonia.

10. The process of claim 1, wherein between approximately 1 and 5 equivalents of acyl bromide or chloride are combined with the nucleoside.

11. The process of claim 1, wherein between approximately 2 and 3 equivalents of acyl bromide or chloride are combined with the nucleoside.

12. The process of claim 1, wherein between approximately 0.5 and 5 equivalents of HX are added.

13. The process of claim 1, wherein between approximately 1 and 3 equivalents of HX are added.

* * * * *